US005759818A

United States Patent [19]

Boime

[11] Patent Number: 5,759,818
[45] Date of Patent: Jun. 2, 1998

[54] N-TERMINAL CTP EXTENDED PHARMACEUTICAL PEPTIDES AND PROTEINS

[75] Inventor: Irving Boime, St. Louis, Mo.

[73] Assignee: Washington University, St. Louis, Mo.

[21] Appl. No.: 485,692

[22] Filed: Jun. 7, 1995

Related U.S. Application Data

[63] Continuation of Ser. No. 419,519, Apr. 10, 1995, which is a continuation-in-part of Ser. No. 771,262, Oct. 4, 1991.

[51] Int. Cl.$^6$ .................. C12N 15/62; C12N 15/19; C12N 15/24; A61K 38/24

[52] U.S. Cl. .................. 435/69.7; 435/69.52; 435/69.5; 435/172.3; 435/325; 435/365.1; 435/252.3; 435/320.1; 424/85.1; 424/85.2; 424/192.1; 530/350; 530/351; 530/398; 536/23.4; 930/110; 930/141; 935/10

[58] Field of Search .................. 530/350, 351, 530/395, 398, 399; 435/69.4, 69.5, 69.52, 172.1, 172.3, 325, 360, 365.1, 320.1, 252.3, 69.7; 935/10–13; 424/2, 12, 85.1, 85.2, 192.1; 536/23.4; 930/110, 141

[56] References Cited

U.S. PATENT DOCUMENTS

| | | | |
|---|---|---|---|
| 4,400,316 | 8/1983 | Katsurgi | 530/398 |
| 4,654,324 | 3/1987 | Chance et al. | 514/12 |
| 4,923,805 | 5/1990 | Reddy et al. | 435/69.4 |
| 4,959,455 | 9/1990 | Clark et al. | 530/351 |
| 5,177,193 | 1/1993 | Boime et al. | 530/397 |
| 5,216,126 | 6/1993 | Cox et al. | 530/350 |
| 5,217,881 | 6/1993 | Park | 435/69.5 |
| 5,338,835 | 8/1994 | Boime | 530/398 |

FOREIGN PATENT DOCUMENTS

| | | |
|---|---|---|
| WO 85/01959 | 9/1985 | WIPO. |
| 86/04589 | 8/1986 | WIPO. |
| 90/09800 | 9/1990 | WIPO. |
| WO 93/06844 | 4/1993 | WIPO. |

OTHER PUBLICATIONS

Davis, C.G. et al., *J. Biol. Chem.*, 261(6):2828 (1986).
Goochee, C.F. et al., *Biotechnology*, (1991) 9:1347.
Kessler, M.J. et al., *J. Biol. Chem.* 254(16):7909 (1979).
LaPolt, P.S. et al., "Enhanced Stimulation of Follicle Maturation and Ovulatory Potential by Long Acting Follicle–Stimulating Hormone Agonists with Extended Carboxyl–Terminal Peptides," *Endocrinology* 131:2514–2520 (1992).
Boime, I. et al. "Structure–function studies of gonadotropins using site–directed mutagenesis and gene transfer: design of a long–acting follitropin agonist," *Chemical Abstracts* 123:127 Abstract 123:1188n 1995.
Fares, F. A. et al. "Design of a long–acting follitropin agonist by fusing the C–terminal sequence of the chorionic gonadotropin beta subunit to the follitropin subunit" *Proc. Natl. Acad. Sci. USA* 89(10):4304–4308 May 1992.

*Primary Examiner*—Lorraine M. Spector
*Attorney, Agent, or Firm*—Morrison & Foerster

[57] ABSTRACT

"Partial" and "complete" CTP units are used to modify biologically active proteins and peptides at the aminoterminus to alter their clearance patterns. "Complete" CTP units have the amino acid sequence found at positions 112–118 to position 145 of the β-subunit of human chorionic gonadotropin; "partial" CTP units are missing at least one amino acid in the region of position 118–145 inclusive. Variants of these CTP units contain 1–5 conservative amino acid substitutions which do not destroy activity. Suitable peptides or proteins which may be modified in this manner include various hormones and cytokines.

17 Claims, 12 Drawing Sheets

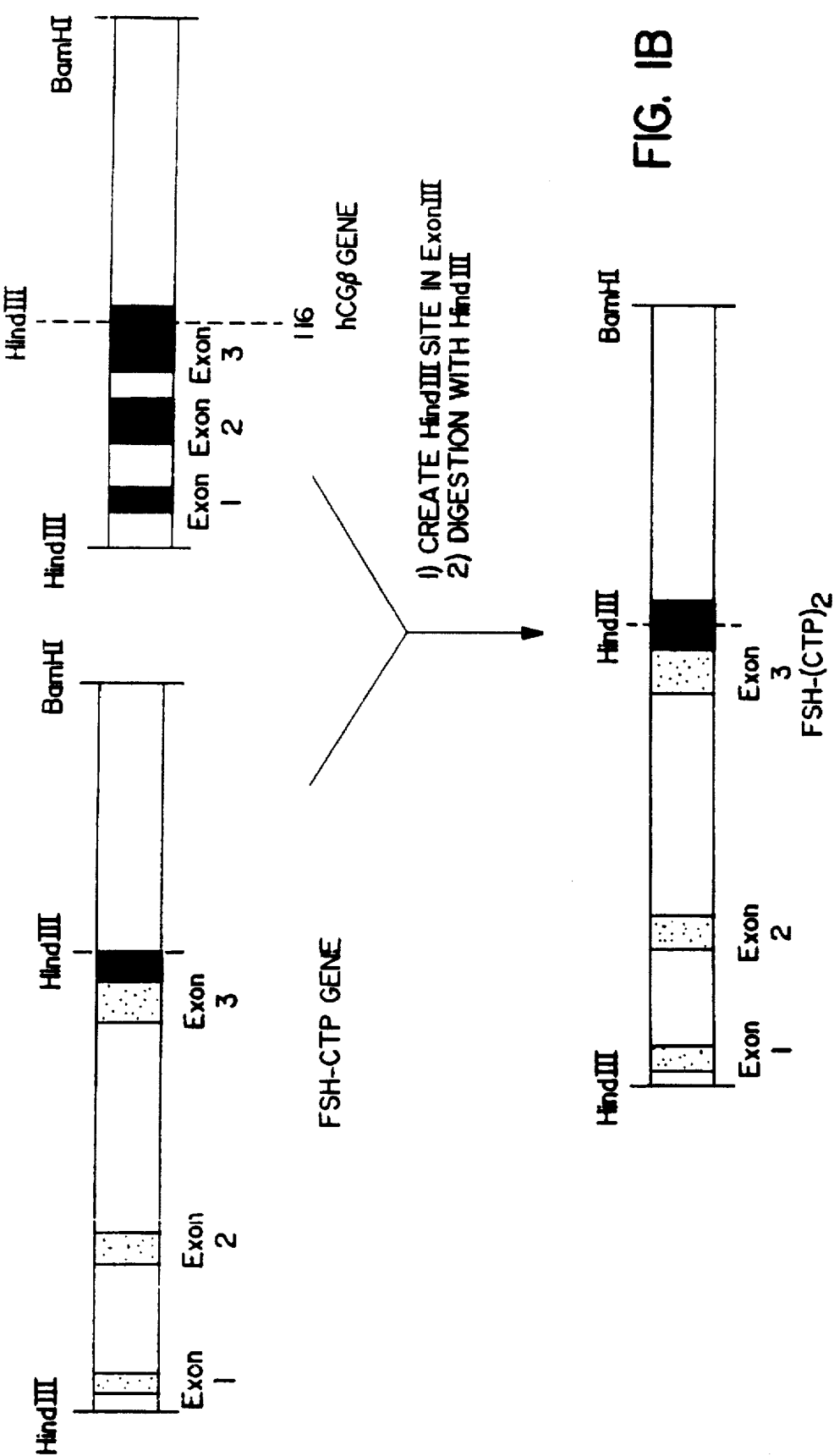

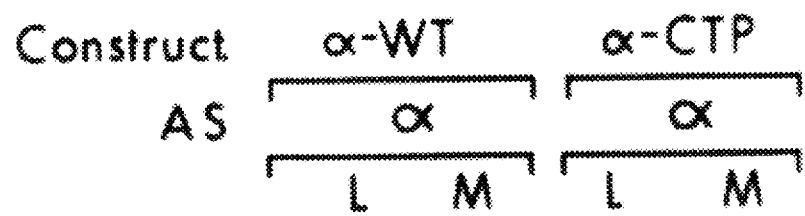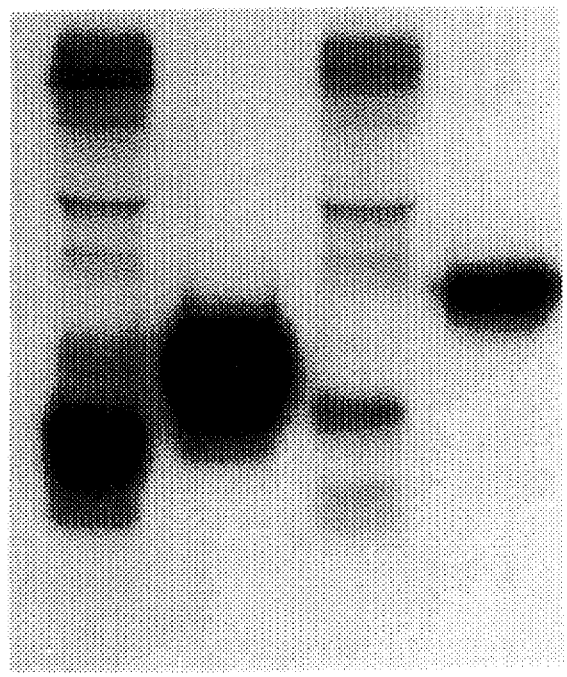
FIG. 7

2

N-TERMINAL CTP EXTENDED PHARMACEUTICAL PEPTIDES AND PROTEINS

CROSS-REFERENCE TO RELATED APPLICATION

This application is a continuation of application Ser. No. 08/419,519 filed 10 Apr. 1995 and now pending; which is a continuation-in-part of application Ser. No. 771,262 filed 04 Oct. 1991.

ACKNOWLEDGMENT OF GOVERNMENT SUPPORT

This invention was made with government support under NIH Contract No. NO1-HD-9-2922, awarded by the National Institutes of Health. The government has certain rights in this invention.

TECHNICAL FIELD

The invention relates to the field of administration of peptide and protein biologically active pharmaceuticals. More particularly, the invention concerns the use of modified peptides and proteins which contain extensions representing the carboxy terminal peptide of human chorionic gonadotropin or fragments thereof.

BACKGROUND ART

PCT application WO 90/09800, published 7 Sep. 1990, describes a number of modified forms of reproductive hormones. As described in the PCT application, any biologically active protein, such as a hormone, a cytokine, a hormone regulator and the like, can be modified so as to improve its clearance characteristics by providing it with an extended amino acid sequence at its carboxy terminus wherein the extension is the carboxy terminal peptide of human chorionic gonadotropin or a variant thereof. As described in this application, the required positions for the carboxy terminal peptide (CTP) are from any one of positions 112–118 to position 145 of the β subunit of human chorionic gonadotropin. As further explained in the PCT application, variants of the CTP extension are obtained by conservative amino acid substitutions such that the capacity of the CTP to alter the clearance characteristics is not destroyed. Fragments shorter than the sequence extending from positions 112–118 to 145 are not specifically disclosed, nor are extensions from other than the C-terminus.

The results specifically with CTP-extended β subunit of FSH are also described in two papers by Applicants herein: LaPolt, P. S. et al.; *Endocrinology* (1992) 131:2514–2520 and Fares, F. A. et al.; *Proc Natl Acad Sci USA* (1992) 89:4304–4308. Both of these papers are incorporated herein by reference.

It has now been found that the alteration of the clearance properties desired can be achieved when the CTP is appended to the N-terminus instead of to the C-terminus of the unmodified peptide or appended to both, or placed in any noncritical region of the peptide, and that this effect may also be achieved using only portions or fragments of the CTP which must, however, contain at least one O-glycosylation site. The desired effects are retained when tandem extensions are employed.

DISCLOSURE OF THE INVENTION

The invention provides modified forms of proteins and peptides that have biological activity, which modified forms have altered clearance properties more desirable than those of the unmodified peptide or protein. The modification comprises providing an additional amino acid sequence in a noncritical region of the peptide or protein, including at the N-terminus or C-terminus or at both termini wherein the extension comprises at least one CTP-derived sequence. The CTP-derived sequence is the native amino acid sequence at positions 112–118 to 145 or variant thereof as herein defined, and must either be only a fragment of this sequence or a tandem form of the sequence when only the carboxy terminus of the peptide is thus extended.

Thus, in one aspect, the invention is directed to a modified protein or peptide pharmaceutical wherein the modification comprises an extension of or insertion into the amino acid sequence of the protein or peptide, said insertion or extension consisting essentially of at least one sequence representing the carboxy terminal peptide (CTP) of human chorionic gonadotropin β-subunit or its variant, or a portion thereof containing at least one O-glycosylation site. Said portion contains at least one amino acid less than the amino acid sequence 118–145 of said CTP. If only the C-terminus of the biologically active peptide or protein is extended, said extension must consist essentially of said portion, rather than the entire CTP unit.

In other aspects, the invention is directed to recombinant materials and methods to produce the modified proteins and peptides of the invention and to pharmaceutical compositions containing them.

BRIEF DESCRIPTION OF THE DRAWINGS

FIGS. 1A and 1B show the construction of a human FSHβ subunit extended by one or two CTP units respectively.

FIG. 7 is a photocopy of SDS-PAGE results obtained from labeled lysates and media of CHO cells transfected with expression vectors for native α subunit and αC.

MODES OF CARRYING OUT THE INVENTION

Figure 1A:
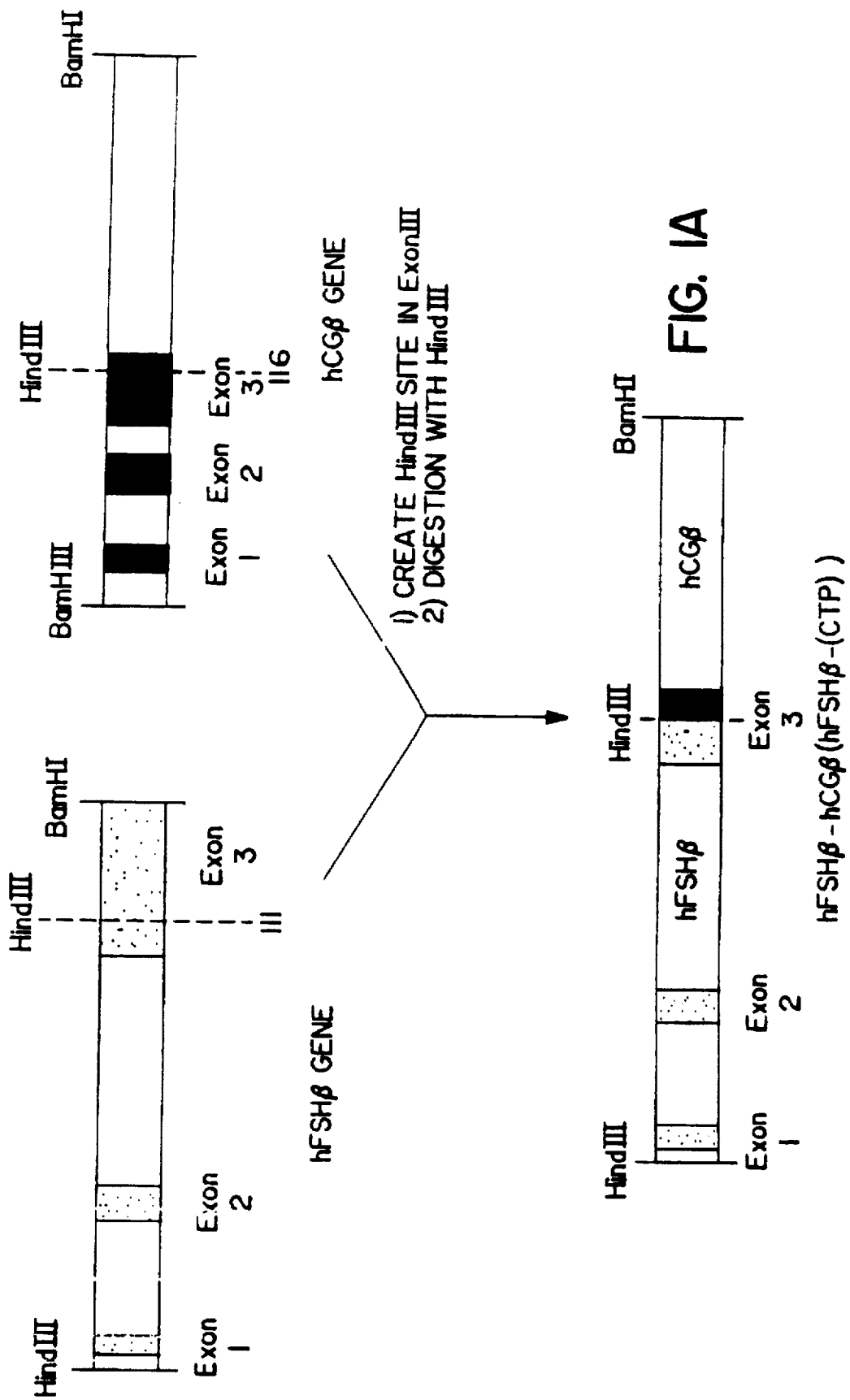
Figure 1C:
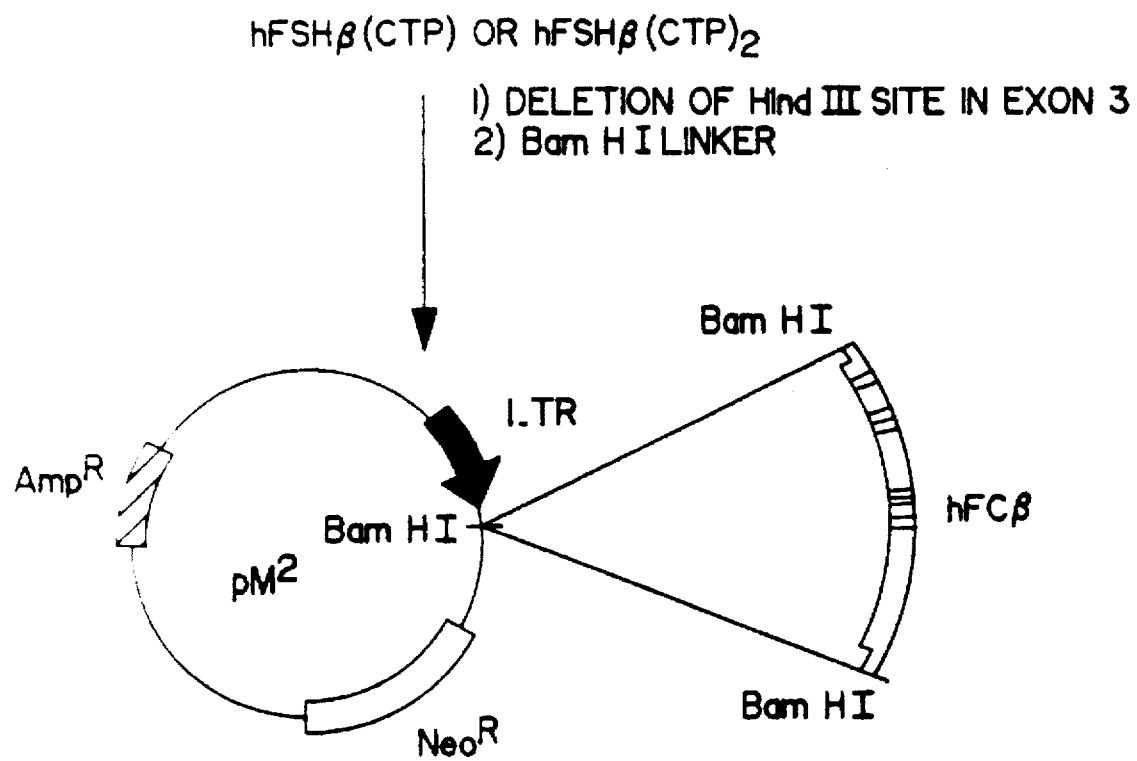
FIG. 1C shows the insertion of the extended FSHβ subunit into the expression vector $pM^2$.
Figure 2:
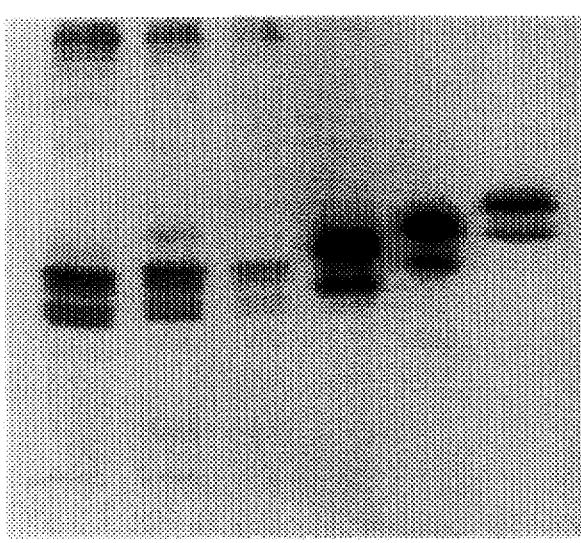
FIG. 2 is a photocopy of the gel obtained form SDS-PAGE conducted on immunoprecipitates of lysates and media of CHO cells containing expression vectors for native and truncated forms of human CGβ.

Human chorionic gonadotropin (hCG) is one of at least four "reproductive" hormones in a family which also includes follicle stimulating hormone (FSH), luteinizing hormone (LH), and thyroid stimulating hormone (TSH). All of these hormones are comprised of α subunits which, for a given species, are identical in amino acid sequence among the group, and β subunits which differ according to the member of the family. The β subunit of hCG is substantially larger than the other β subunits in that it contains approximately 34 additional amino acids at the C-terminus referred to herein as the carboxy terminal portion (CTP) which is considered responsible for the comparatively longer serum half-life of hCG as compared to other gonadotropins (Matzuk, M. et al., Endocrinol (1989) 126:376). In the native hormone, this CTP extension contains four mucin-like O-linked oligosaccharides.

As used herein, human alpha subunit, and human FSH, LH, TSH, and CG beta subunits as well as the heterodimeric forms have in general their conventional definitions and refer to the proteins having the amino acid sequences known in the art per se, or allelic variants thereof, deliberately constructed muteins thereof maintaining the activity of the native protein regardless of the glycosylation pattern exhibited, or mutant forms thereof having at least 90% homology, preferably 95% homology, with the native forms.

"Native" forms of these peptides are those which have the amino acid sequences isolated from human tissue, and have these known sequences per se, or their allelic variants.

"Mutein" forms of these proteins are those which have deliberate alterations in amino acid sequence produced by, for example, site-specific mutagenesis or by other recombinant manipulations, or which are prepared synthetically. These alterations result in amino acid sequences wherein the biological activity of the subunit is retained and/or wherein the subunit has at least 90% homology, preferably 95% homology, with the native form.

Although it is recognized that glycosylation pattern has a profound influence on activity both qualitatively and quantitatively, for convenience the terms FSH, LH, TSH, and CG beta subunits refers to the amino acid sequence characteristic of the peptides, as does "alpha subunit." When only the beta chain is referred to, the terms will be, for example, FSH beta; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

As used herein "peptide" and "protein" are used interchangeably, since the length distinction between them is arbitrary.

"Noncritical" regions of peptides or proteins are those regions of the molecules not required for maximal biological activity. In general, these regions are distant from binding sites, precursor cleavage sites, and catalytic regions.

Figure 10:
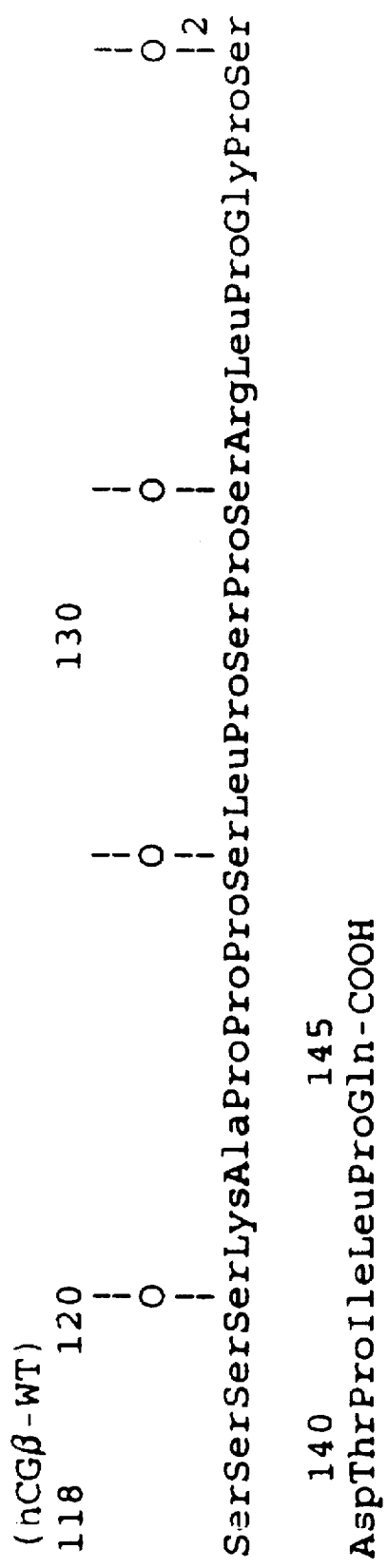
FIG. 10 SEQ ID No: 13 shows the amino acid sequence and numbering of positions 112–145 of human CGβ.

As used herein, the "CTP unit" refers to an amino acid sequence found at the carboxy terminus of human chorionic gonadotropin β subunit which extends from amino acid 112–118 to residue 145 at the C-terminus or to a portion thereof. Thus, each "complete" CTP unit contains 28–34 amino acids, depending on the N-terminus of the CTP. The native sequence of positions 112–145 is shown in FIG. 10.

By a "partial" CTP unit is meant an amino acid sequence which occurs between positions 112–118 to 145 inclusive, but which has at least one amino acid deleted from the shortest possible "complete" CTP unit (i.e. from positions 118–145). The "partial" CTP units included in the invention must contain at least one O-glycosylation site. The CTP unit contains four such sites at the serine residues at positions 121 (site 1); 127 (site 2); 132 (site 3); and 138 (site 4). The partial forms of CTP useful in the invention will contain one or more of these sites arranged in the order in which they appear in the native CTP sequence. Thus, the "partial" CTP unit useful in the invention may include all four glycosylation sites; sites 1, 2 and 3; sites 1, 2 and 4; sites 1, 3 and 4; sites 2, 3 and 4; or simply sites 1 and 2; 1 and 3; 1 and 4; 2 and 3; 2 and 4; or 3 and 4; or may contain only one of sites 1, 2, 3 or 4.

By "tandem" extensions is meant that the insert or extension contains at least two "CTP units". Each CTP unit may be complete or a fragment, and native or a variant. All of the CTP units in the tandem extension or insert may be identical, or they may be different from each other. Thus, for example, the tandem extension or insert may generically be partial-complete; partial-partial; partial-complete-partial; complete-complete-partial, and the like wherein each of the noted partial or complete CTP units may independently be either a variant or the native sequence. The nature of variants is further explained below.

Variants

The "CTP unit" may correspond exactly to the native CTP sequence, or may be a variant wherein 1–5 of the amino acids contained in the sequence is substituted by a conservative analog of the native amino acid residue at that position, and wherein said substitutions taken cumulatively do not result in a substantial change in the stability conferring properties of the CTP unit. "Conservative analog" means, in the conventional sense, an analog wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89–99. In general, acidic amino acids fall into one group; basic amino acids into another; neutral hydrophilic amino acids into another; and so forth.

More specifically, amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows:

Acidic: Aspartic acid and Glutamic acid;

Basic/noncyclic: Arginine, Lysine;

Basic/cyclic: Histidine;

Neutral/polar/small: Glycine, serine, cysteine;

Neutral/nonpolar/small: Alanine;

Neutral/polar/large /nonaromatic: Threonine, Asparagine, Glutamine;

Neutral/polar/large aromatic: Tyrosine;

Neutral/nonpolar/large/nonaromatic: Valine, Isoleucine, Leucine, Methionine;

Neutral/nonpolar/ large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

If the modified peptides of the invention are constructed by modification of the gene, the CTP units will contain only gene encoded amino acid substitutions; however, if the CTP unit is synthesized by standard, for example, solid phase, peptide synthesis methods and ligated, for example, enzymatically, to the C-terminus of the acceptor peptide or protein, non-gene encoded amino acids, such as aminoisobutyric acid (Aib), phenylglycine (Phg), and the like can also be substituted for their analogous counterparts.

These non-encoded amino acids also include, for example, beta-alanine (beta-Ala), or other omega-amino acids, such as 3-amino propionic, 4-amino butyric and so forth, sarcosine (Sar), ornithine (Orn), citrulline (Cit), t-butylalanine (t-BuA), t-butylglycine (t-BuG), N-methylisoleucine (N-MeIle), and cyclohexylalanine (Cha), norleucine (Nle), cysteic acid (Cya) 2-naphthylalanine (2-Nal); 1,2,3,4-tetrahydroisoquinoline-3-carboxylic acid (Tic); mercaptovaleric acid (Mvl); β-2-thienylalanine (Thi); and methionine sulfoxide (MSO). These also fall conveniently into particular categories.

Based on the above definitions,

Sar and beta-Ala and Aib are neutral/nonpolar/ small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/large/ nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4-aminobutyric) or large (all others).

Thus, amino acid substitutions other than those encoded in the gene can also be included in peptide compounds within the scope of the invention and can be classified within this general scheme according to their structure.

Preferred Embodiments of CTP Units

The notation used for the CTP units of the invention is as follows: for portions of the complete CTP unit, the positions included in the portion are designated by their number as they appear in FIG. 10 herein. Where substitutions occur, the substituted amino acid is provided along with a superscript indicating its position. Thus, for example, CTP (120–143) represents that portion of CTP extending from positions 120 to 143; CTP (120–130; 136–143) represents a fused amino acid sequence lacking positions 118–119, 131–135, and 144–145 of the native sequence. CTP (Arg$^{122}$) refers to a variant wherein the lysine at position 122 is substituted by an arginine; CTP (Ile$^{134}$) refers to a variant wherein the leucine at position 134 is substituted by isoleucine. CTP (Val$^{128}$ Val$^{143}$) represents a variant wherein two substitutions have been made, one for the leucine at position 128 and the other for the isoleucine at position 142. CTP (120–143; Ile$^{128}$ Ala$^{130}$) represents the relevant portion of the CTP unit where the two indicated substitutions have been made.

Particularly preferred are those CTP units of the following formulas:

1 CTP (116–132)
2 CTP (118–128; 130–135)
3 CTP (117–142)
4 CTP (116–130)
5 CTP (116–123; 137–145)
6 CTP (115–133; 141–145)
7 CTP (117–140, Ser$^{123}$ Gln$^{140}$)
8 CTP (125–143, Ala$^{130}$)
9 CTP (135–145, Glu$^{139}$)
10 CTP (131–143, Mvl$^{142}$ Cha$^{143}$)
11 CTP (118–132)
12 CTP (118–127)
13 CTP (118–145)
14 CTP (115–132)
15 CTP (115–127)
16 CTP (115–145)
17 CTP (112–145)
18 CTP (112–132)
19 CTP (112–127)

Modified Peptides and Proteins

Any peptide or protein of biological significance is subject to modification according to the invention method. Included among such candidates for modification, therefore, are peptide hormones, such as the four human "reproductive" hormones set forth above, including the β-chains thereof; insulin; human growth hormone and growth hormone of other species; enkephalin; ACTH; glucagon; and the like. Also useful as subjects for the modification of the invention are various growth factors such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Enzymes such as tPA (which has a very short half life), urokinase and thrombin may also be modified. Also candidates for the method of the invention are short peptide sequences such as luteinizing hormone releasing hormone (LHRH); somatostatin; growth hormone releasing factor (GHRF); and the endorphins. Additional protein medicaments such as alveolar surfactant proteins; natriuretic factors; erythropoietin, adhesions; receptor peptides; receptor binding ligands in general; antibodies and fragments thereof; and any other useful peptide or protein with a desired biological function can be modified according to the methods described herein.

It should be noted, of course, that the peptide or protein into which the CTP unit(s) is(are) inserted or to which the CTP unit(s) is(are) added as an extension could also be in modified form from that ordinarily occurring biologically, as long as biological activity is retained.

A particularly preferred candidate for modification with the CTP units of the invention is the α subunit of the reproductive hormones. This has the advantage that coupling of the modified α subunit with the corresponding β units results in an entire set of hormones for which bioactivity can be extended. The CTP unit or tandem units may be fused at either or both of the carboxy or amino terminus of the α subunit; however, the amino terminus is preferred. Available evidence shows that the amino terminus is not significantly involved in assembly with the β subunit nor is it associated with receptor binding determinants.

As set forth above, the insertions or extensions of the CTP unit(s) must be in a region of the peptide or protein that is noncritical for the biological activity desired. Thus, regions critical for inducing proper folding, binding to receptors, catalytic activity and the like should be avoided. Similarly, regions which are critical to assure the three-dimensional conformation of the protein should be avoided. The ascertainment of noncritical regions is readily accomplished by deleting or modifying candidate regions and conducting an appropriate assay for the desired activity. Regions where modifications result in loss of activity are critical; regions wherein the alteration results in the same or similar activity are considered noncritical.

In many cases, the locations of critical regions are known. For example, for the α-subunit, position 33–59 are thought to be necessary for signal transduction and the 20 amino acid stretch at the carboxy terminus is needed for signal transduction/receptor binding. Residues critical for assembly with the β-subunit include at least residues 33–58, particularly 37–40.

If the protein or peptide candidate has not been studied adequately, as set forth above, noncritical regions may be ascertained by deleting or modifying candidate regions in conducting an appropriate assay for the desired activity. An appropriate starting point for proteins in general is at the N- or C- terminus; however, in some particular cases, these starting points will not necessarily yield successful results. In addition to the N-terminus and C-terminus per se, insertion in regions close to these termini also represents reasonable starting points. In order for the insertion of the CTP unit or portion thereof, some small number of amino acids may be deleted from the noncritical region. Preferred embodiments of the modified proteins and peptides of the invention include the following:

CGα (1–3)-CTP#1-(4–92)
CGα (1–3)-CTP#11-(4–92)
CGα (1–3)-CTP#12-(4–92)
CGα (1–92)-CTP#11
CGα (1–92)-CTP#12
CGα (1–3)-CTP#17(4–92)
CGα (1–3)-CTP#18(4–92)
CGα (1–3)-CTP#19(4–92)
FSHβ (1–111)-CTP#11
FSHβ (1–111)-CTP#12
FSHβ (1–111)-CTP#11-CTP#12
proinsulin (1–3)-CTP#5-CTP#6 (4–end)
FSHβ (1–111)-CTP#13-CTP#13
TSHβ (1–110)-CTP#11
TSHβ (1–110)-CTP#12
LHβ (1–110)-CTP#14
LHβ (1–114)-CTP#15
LHβ (1–114)-CTP#16
LHβ (1–114)-CTP#11
LHβ (1–121)-CTP#12
LHβ (1–121)-CTP#13
tPA (1–2)-CTP#14 (3–end)
tPA (1–2)-CTP#15 (3–end)
tPA (1–2)-CTP#16 (3–end)
hGH (1–4)-CTP#11 (5–end)
hGH (1–4)-CTP#12 (5–end)
hGH (1–4)-CTP#13 (5–end)
IL-3 (1–end)-CTP#14
IL-3 (1–end)-CTP#15
IL-3 (1–end)-CTP#16

Coupled Forms

The modified peptides and proteins of the invention may be further conjugated or derivatized in ways generally understood to derivatize amino acid sequences, such as phosphorylation, glycosylation, deglycosylation of ordinarily glycosylated forms, modification of the amino acid side chains (e.g., conversion of proline to hydroxyproline) and similar modifications analogous to those post-translational events which have been found to occur generally.

As is generally known in the art, the modified peptides and proteins of the invention may be coupled to labels, drugs, targeting agents, carriers, solid supports, and the like, depending on the desired application. The labeled forms of the modified biologicals may be used to track their metabolic fate; suitable labels for this purpose include, especially, radioisotope labels such as iodine 131, technetium 99, indium 111, and the like. The labels may also be used to mediate detection of the modified proteins or peptides in assay systems; in this instance, radioisotopes may also be used as well as enzyme labels, fluorescent labels, chromogenic labels, and the like. The use of such labels is particularly helpful if the peptide or protein is itself a targeting agent such as an antibody or a receptor ligand.

Conversely, if the modified peptide or protein is a targeting ligand, primarily, and is relatively free of metabolism-altering activity, the modified compound of the invention may be conjugated to an appropriate drug, such as an antiinflammatory drug, an antibiotic, a toxin, and the like. The modified compounds of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the modified peptides and proteins of the invention to solid supports. When coupled, these modified peptides and proteins can then be used as affinity reagents for the separation of desired components with which specific reaction is exhibited.

Preparation Methods

Methods to construct the modified peptide and protein biologically active compounds of the invention are well known in the art. As set forth above, if only gene encoded amino acids are included, the most practical approach at present is to synthesize these materials recombinantly by modification of the DNA encoding the desired peptide. Techniques for site-directed mutagenesis, ligation of additional sequences, and construction of suitable expression systems are all, by now, well known in the art. The DNA encoding the CTP unit(s) to be added to the DNA encoding the desired peptide or protein is most conveniently constructed synthetically using standard solid phase techniques, preferably to include restriction sites for ease of ligation, and coupled to the sequence encoding the candidate peptide or protein. If the DNA encoding the candidate peptide or protein is not already a part of an expression system containing suitable control elements for transcription and translation of the included coding sequence, the modified DNA coding sequences are provided with these features. As is well known, expression systems are now available compatible with a wide variety of hosts, including procaryotic hosts such as bacteria and eucaryotic hosts such as yeast, plant cells, insect cells, mammalian cells, avian cells, and the like.

When the unmodified peptide is a reproductive hormone including the α-subunit, whether the α-subunit is modified or unmodified, recombinant production of the appropriate α-subunit is preferably effected using a "minigene" construction.

As used herein, the alpha subunit "minigene" refers to the gene construction disclosed in Matzuk, M. M., et al, *Mol Endocrinol* (1988) 2:95–100, in the description of the construction of pM²/CG alpha or pM²/alpha. This "minigene" is characterized by retention only of the intron sequence between exon III and exon IV, all upstream introns having been deleted. In the particular construction described, the N-terminal coding sequences which are derived from exon II and a portion of exon III are supplied from cDNA and are ligated directly through an XbaI restriction site into the coding sequence of exon III so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the alpha subunit which retain the intron between exons III and IV, or any other intron, and preferably no other introns, i.e. only one intron need be in the sequence.

For recombinant production, transfected host cells using expression systems are used and cultured to produce the desired protein. These terms are used herein as follows:

A "transfected" recombinant host cell, i.e., a cell "transfected" with the recombinant expression systems of the invention, refers to a host cell which has been altered to contain this expression system by any convenient manner of introducing it, including transfection, viral infection, and so forth. "Transfected" refers to cells containing this expression system whether the system is integrated into the chromosome or is extrachromosomal. The "transfected" cells may either be stable with respect to inclusion of the expression system or not. In short, "transfected" recombinant host cells with the expression system of the invention refers to cells which include this expression system as a result of their manipulation to include it, when they natively do not, regardless of the manner of effecting this incorporation.

"Expression system" refers to a DNA sequence which includes a coding sequence to be expressed and those accompanying control DNA sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

Alternatively, if the candidate biological is a short peptide or if enzymatic transfer of the subunit can be effected, the CTP unit(s) of the invention may be synthesized directly using in vitro solid phase peptide synthesis techniques and under these conditions, if desired, the CTP subunit may be modified by analogous amino acids which are not gene encoded.

Antibodies

The modified peptides and proteins of the invention may be used to generate antibodies specifically immunoreactive with these new compounds. These antibodies are useful in a variety of diagnostic and therapeutic applications, depending on the nature of the biological activity of the unmodified peptide or protein.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the modified peptides of the invention.

By "immunospecific for the modified peptides" is meant antibodies which are immunoreactive with the CTP-unit-modified forms of the peptides or proteins, but not with the unmodified portions within the general parameters considered to determine affinity or nonaffinity. It is understood that specificity is a relative term, and an arbitrary limit could be chosen, such as a difference in immunoreactivity of 100-fold or greater. Thus, an immunospecific antibody included within the invention is at least 100 times more reactive with the modified protein or peptide than with its unmodified form.

Formulation

The modified peptides or proteins of the invention are formulated and administered using methods comparable to those known for the unmodified peptide or protein corresponding to the modified form. Thus, formulation and administration methods will vary according to the candidate unmodified form. However, the dosage level and frequency of administration may be reduced as compared to the unmodified form in view of the extended biological half life of the modified peptide or protein.

Formulations for the peptides and proteins modified according to the invention are those typical of protein or peptide drugs such as found in *Remington's Pharmaceutical Sciences*, latest edition, Mack Publishing Company, Easton, Pa. Generally, proteins or peptides are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches.

Oral administration is also possible provided the formulation protects the peptides of the invention from degradation in the digestive system.

Figure 3:
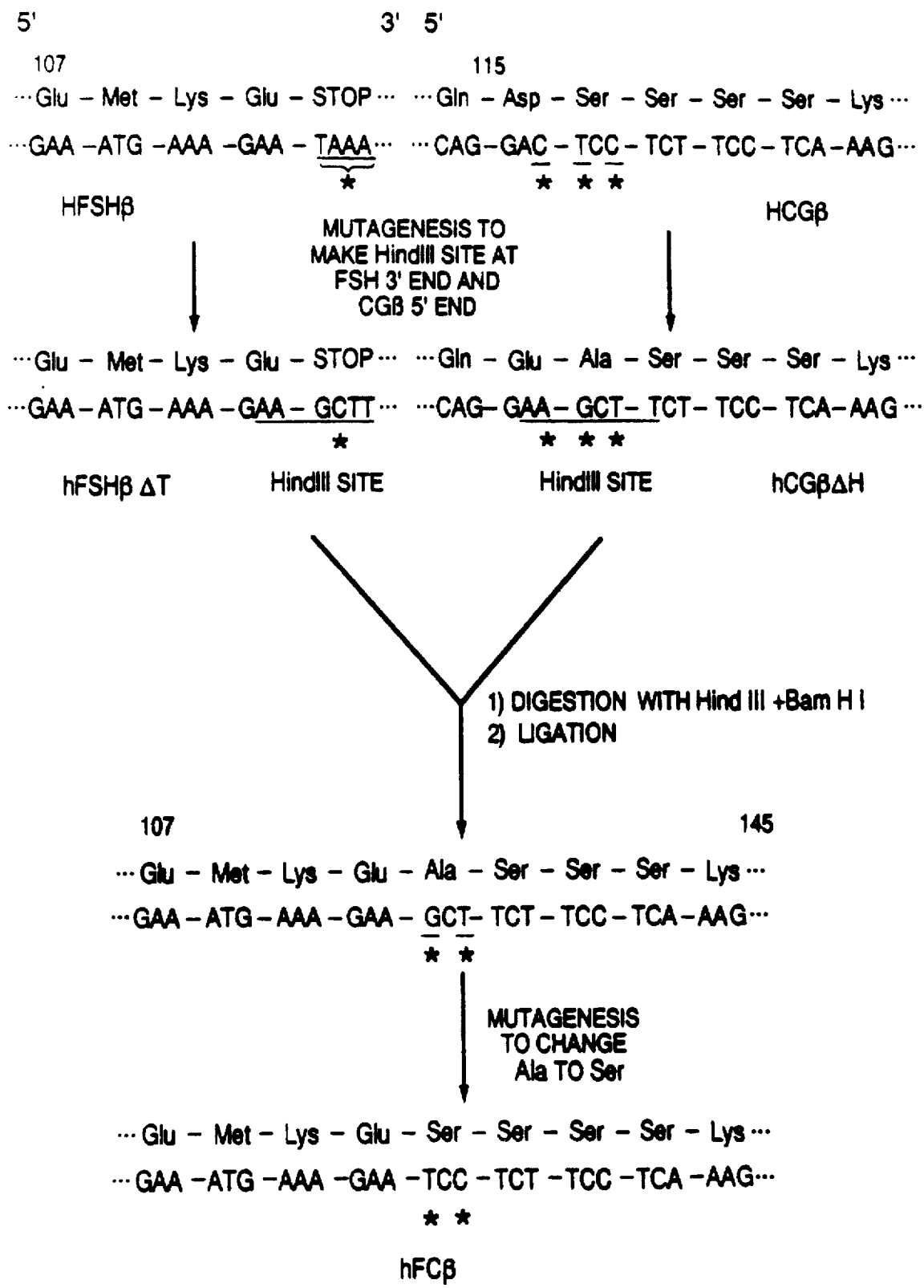
FIG. 3 (SEQ ID No: 1 SEQ ID No: 12 ) shows the details of the fusion of a single CTP unit representing positions 115–145 to the carboxy terminus of FSHβ as described in FIG. 1A.

Optimization of dosage regimen and formulation is conducted as a routine matter and as generally performed in the art.

The following examples are intended to illustrate but not to limit the invention.

EXAMPLE 1

Preparation of Human β Subunit with Two CTP Unit Tandem Extensions

FIGS. 1A and 1B show the construction of an expression vector wherein the β-chain of human FSH is modified to include two CTP units. As shown in FIG. 1B, the HindIII site at the 3'-terminus of the human FSHβ subunit, extended by one CTP unit is used to couple the CTP unit from the 3' terminus of the human HCG-β gene to obtain the extended β subunit. The hFSH-β $(CTP)_2$ gene is then ligated into the expression vector $pM^2$ to obtain an expression system capable of producing the extended form of the FSH-β chain in mammalian cells. The construction of the host expression vectors is described by Matzuk, M. M. et al., *Proc Natl Acad Sci USA* (1987) 84:6354–6358; Matzuk, M. M. et al., *J Cell Biol* (1988) 106:1049–1059.

In more detail, to create hFSHβchimera bearing a single unit of the O-linked terminal region of hCGβ subunit hFSHβ (CTP)) a HindIII site was created in the stop codon of hFSHβ gene at codon 111 and in the hCGβ gene at codon 118 (FIG. 1A). The HindIII-HindIII fragment from the hFSHβ gene was ligated in frame to the CGβ BamHI-HindIII fragment. This chimera (hFSHβ(CTP)) contained a $ser^{118}$ to $Ala^{118}$ change at the ligation point, which was corrected by oligonucleotide-directed mutagenesis. The chimera containing two tandem CTP repeats (hFSHβ $(CTP)_2$ was constructed by creating a new HindIII site in the stop codon of the hFSHβ(CTP) chimera (FIG. 1B). The HindIII-HindIII fragment was ligated to the BamHI-HindIII fragment from hCGβ. The generated ala codon can be reconverted to a serine codon as described above.

To insert hFSHβ(CTP) or hFSHβ$(CTP)_2$ genes into he eucaryotic expression vector $pM^2$, the HindIII sites at the 5' ends were converted to BamHI sites using Klenow and BamHI oligonucleotide linker (FIG. 1C), and the BamHI-BamHI fragments containing the hFSHβCTP or hFSHβ $(CTP)_2$ genes were inserted into the BamHI site in $pM^2$. The correct orientation was confirmed by restriction enzyme analysis and the entire sequence of exon III was sequenced to confirm the specificity of the mutagenesis.

EXAMPLE 2

Effect of CTP Tandem Extensions

The human FSH containing the β subunit extended by two CTP units prepared as set forth in Example 1 above was injected into rats. 24 Sprague-Dawley female rats were used in the study. 12 rats were each injected with 10 IU unmodified FSH formulated in MEM medium; 12 rats were injected with 10 IU FSH comprising hFSHβ$(CTP)_2$ formulated in MEM medium. Serum was withdrawn immediately and several times during the first hour, and then after 2, 4 and 8 hours. The serum was assayed using standard radioimmunoassay techniques for FSH hormone.

The results showed that while the amount of unmodified FSH in the serum declined from about 0.5 IU/ml to less than 0.05 IU/ml over an 8 hour period, the modified FSH of the invention containing two CTP units remains substantially unchanged over this time period declining from about 0.8 IU/ml to about 0.5 IU/ml.

EXAMPLE 3

Construction of CTP Units that Represent "Partial" Units

The gene encoding human chorionic gonadotropin β subunit is inserted into the plasmid $pM^2$ (supra) at the BamHI site downstream of the long terminal repeat (LTR). A BamHI/BglII) fragment is subcloned into M13 for site-directed mutagenesis. Stop codons are thus provided in place of the arginine residue at position 133 or in place of the leucine residue at position 128. The mutated fragment is then reinserted into the $pM^2$ host vector.

The vectors encoding truncated forms of human CGβ were then transfected into CHO cells and the transfected cells cultured and labeled for 7 hours with $^{35}S$-cysteine. Lysates and media were prepared and immunoprecipitated with CGβ antiserum. The precipitates were then subjected to SDS polyacrylamide gel electrophoresis with results shown in FIG. 2. In FIG. 2, the lysate and media lanes are labeled according to the carboxy terminus. It is well established that the final steps of the serine-O-linked glycosylation occur just prior to secretion. Therefore there is a mobility shift reflecting the increase in molecular weight of the subunit when it is secreted. As seen here, there is a progressive decrease in the molecular weight shift from lysate to medium in the shortened forms of hCGβ. The data show lower molecular weights for the secreted forms of the truncated subunits, thus indicating the absence of serine glycosylation sites.

EXAMPLE 4

Construction of Modified FSHβ And Other Peptides

The CTP unit representing the "complete" form or the "portion" form is then ligated to FSHβ by cleaving both FSHβ and the mutated or unmutated hCGβ gene with HindIII and ligating the resultant upstream portion of FSH with the CTP unit, as shown in FIG. 1A. Religation results in a ser-to-ala substitution at position 118 of the CTP unit.

If desired, this can be reconverted to a codon for serine, as shown in FIG. 3.

Figure 4:
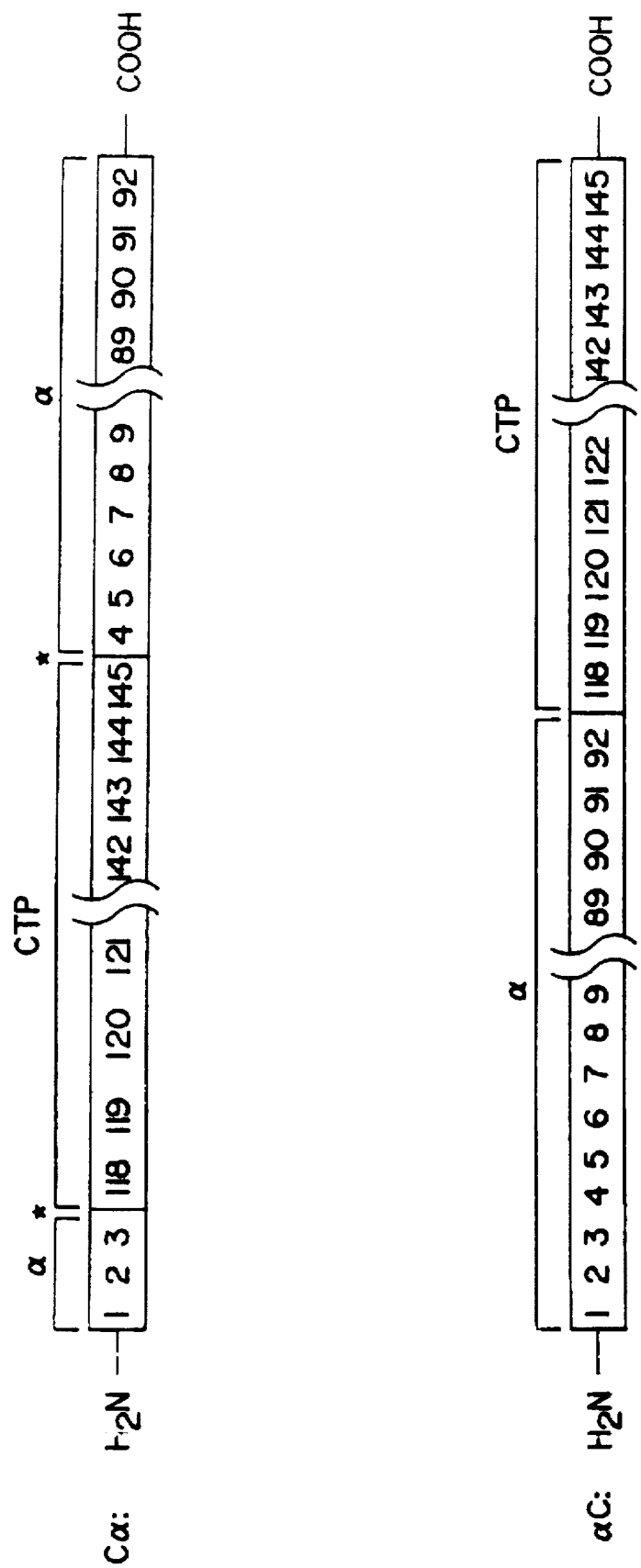
FIG. 4 shows the positions for insertion of a CTP subunit representing positions 118–145 at the amino or carboxy terminus of the α subunit.

Similarly, the C-terminal extended form of human proinsulin, growth hormone, and α-subunit are prepared from the CTP unit in complete or portion forms. The CT unit can be inserted either at the amino or carboxy terminus of the α subunit, as shown in FIG. 4. As there illustrated, positions 118–145 of hCGβ are inserted.

In more detail, to construct chimeras containing the CTP unit "complete" or as a "portion" at the carboxy terminus of the α-subunit (αC), the BamHI-BglIII and HingIII-BamHI fragments containing the alpha subunit and hCGβ genes, respectively, are subjected to the polymerase chain reaction (PCR) (Horton, R. M. et al., Gene (1989) 77:51–59). This is diagramed in FIG. 5. The GH fragment shown, which was transcribed from the α minigene (author) (J Cell Biol (1988) 106:1049–1059) contains the entire translated sequence of the α subunit, and the IJ fragment containing the CTP sequence from the CGβ subunits, were amplified in separate PCR reactions. The 3' end of primer H used to amplify the GH fragment is complementary to the 5' end of the CTP sequence. Similarly, the 5' end of primer I was complementary to the 3' end of α sequence. Thus, by using two internal primers that overlap, the GH and IJ fragments share "sticky ends". These fragments were purified and mixed together and used as a template for PCR. The overlapping ends allow one strand from each fragment to act as a primer on the other and adding G and I primers allows the amplification of the α-CTP chimera gene. The α-CTP gene was inserted into the BamHI site of pM².

The sequences of the primers used in the construction of αC are as follows: (5'→3')

H=GCCTTTGAGGAAGAGGAAGATTTGTGATAATAAC (SEQ. ID No: 14)

I=GTTATTATCACAAATCTTCCTCTTCCTCAAAGGC (SEQ. ID No: 15 )

J=GTAAAACGACGGCCAGT (SEQ. ID No. 16)

G=AACAGCTATGACCATGA (SEQ. ID No. 17)

Oligonucleotides G and J are for priming M13 mp 19 (New England Biolabs 1992, catalogue #1201 and 1211). Oligonucleotides G and J prime downstream and upstream, respectively of the polylinker region.

Figure 5:
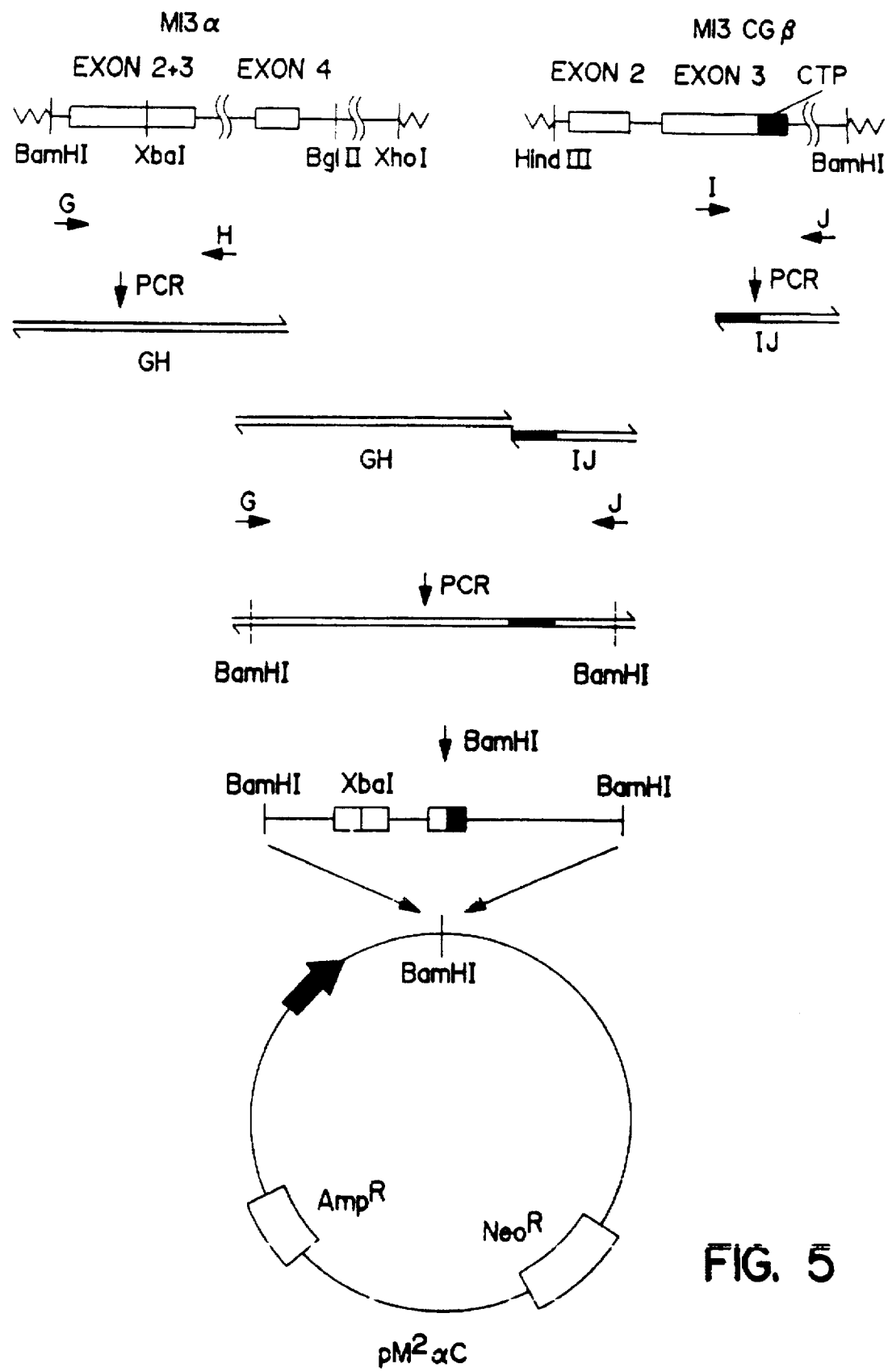
FIG. 5 diagrams the construction of the α subunit extended at the carboxy terminus by CTP (αC).
Figure 6:
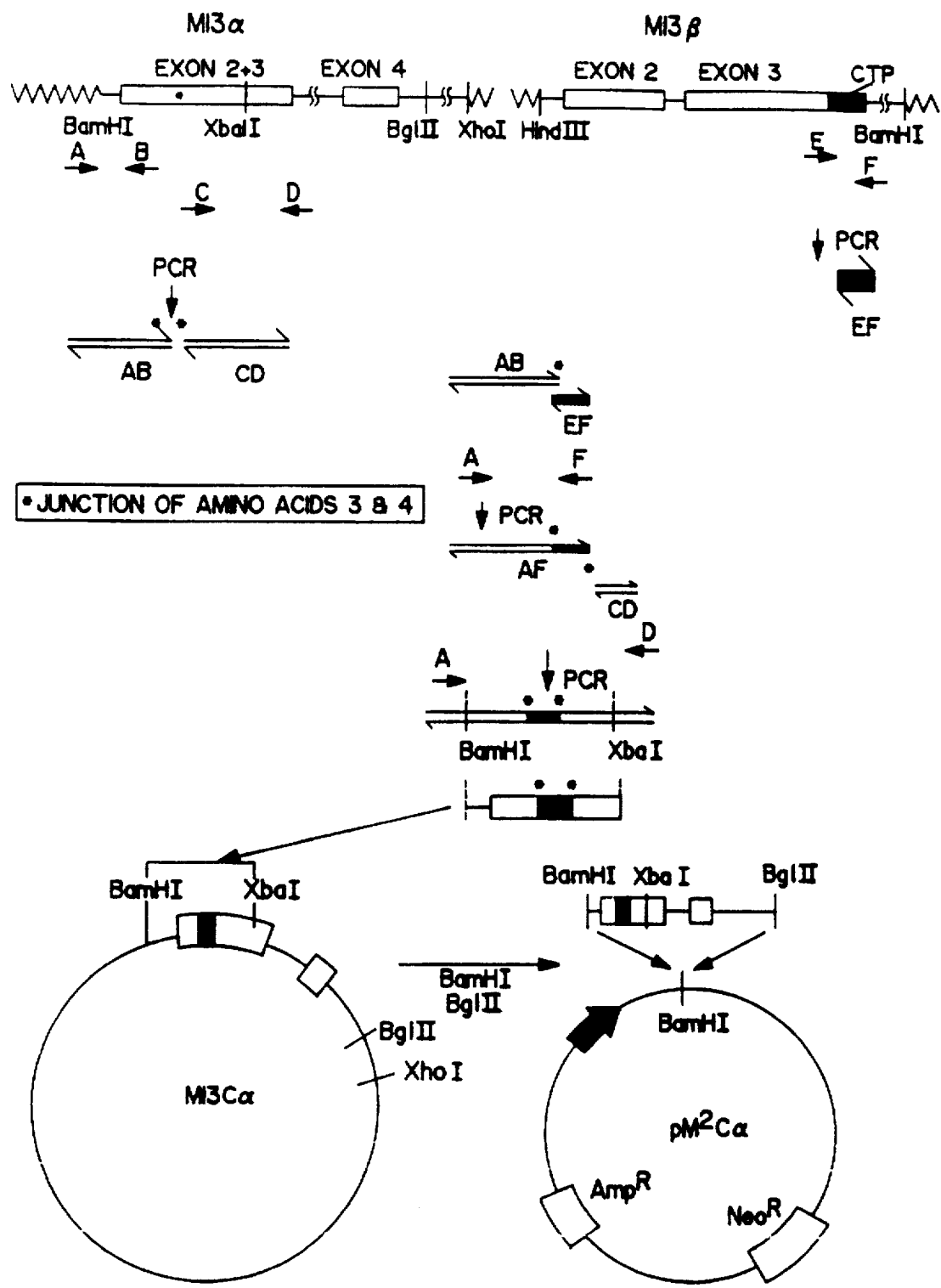
FIG. 6 diagrams the construction of Cα wherein a CTP unit representing positions 118–145 of hCGβ is inserted between amino acids 3 and 4 of the α subunit.

The CTP was also inserted into the N-terminal end of the α subunit at the amino acid ¾ junction (Cα; FIG. 5) in a manner similar to that used for constructing the αC. CTP was inserted in an internal region of the subunit between amino acid 3 and 4 (FIG. 6).

The sequences of the oligonucleotide primers used in the construction of Cα are:

(A) 5'-AGC GGA TAA CAA TTT CAC ACA GGA-3' (SEQ. ID No: 18)

(E) 5'-CAT TCC GCT CCT GAT TCC TCT TCC TCA AAG-3' (SEQ. ID No: 19)

(B) 3'-GTA AGG CGA GGA CTA AGG AGA AGG AGT TTC-5' (SEQ. ID No: 20)

(C) 5'-CCG ATC CTC CCA CAA GTG CAG GAT TGC CCA-3' (SEQ. ID No: 21)

(F) 3'-GGC TAG GAG GGT GTT CAC GTC CTA ACG GGT-5' (SEQ. ID No: 22)

(D) 3'-ATT CTT GGA GTT CTA GGG GTC TTC GAAA-5' (SEQ. ID No: 23)

Oligonucleotides A and D are used to prime M13.

The 5-end of primer B used to amplify the AB fragment provides a sequence complementary to the 5'-end of the CTP region. Similarly, the 5'-end of primer C, used to amplify the cd fragment, is complementary to the 3'-end of the CTP sequence. The fragments were gel purified and mixed for use as a PCR template. The overlapping ends permit one strand from each fragment to act as a primer for the other; adding a and d primers allows amplification of the entire chimera.

Correct orientation was confirmed by restriction enzyme analysis, and the resulting modified gene was sequenced to verify correct substitutions.

EXAMPLE 5

Production of Modified Hormones

The gene encoding the modified α-subunit (αC) was inserted into the BamHI site of pM² and transfected alone or together with the CGβ gene into Chinese hamster ovary cells. Continuous labeling of stable clones with $S^{35}$ cysteine shows that the secreted form of the modified peptide migrates more slowly than the corresponding unmodified form. In FIG. 7, lanes 1 and 3 represent the lysates of cells producing unmodified α-subunit and αC, respectively; lines 2 and 4 are the corresponding supernatants. Since the secreted form of modified αC has a much greater change in mobility with respect to the lysate form as compared to wild type α, it can be concluded that secreted αC contains O-linked oligosaccharides contributed by the CTP extension.

Co-transfection of the FSHβ subunit with either αC or Cα in CHO cells resulted in dimers that were secreted with an efficiency comparable to unmodified recombinant FSH.

EXAMPLE 6

Biological Activity

Wild type recombinant FSH and dimers of FSHβ with αC or Cα were quantitated in conditioned medium with a FSH immunoradiometric assay and a double-antibody RIA (Diagnostic Products, Los Angeles). The in vitro bioactivity of these hormones was determined by the granulosa cell aromatase bioassay as described (Keene, J., et al *J Biol Chem* (1989) 264:4769–4769; Jia, X. C. and Hsueh, A. author *Endocrinology* (1986) 119:1570–1577). Stimulation of estrogen production by unmodified FSH and by αC and Cα FSH was compared after a 3-day culture period.

Figure 8:
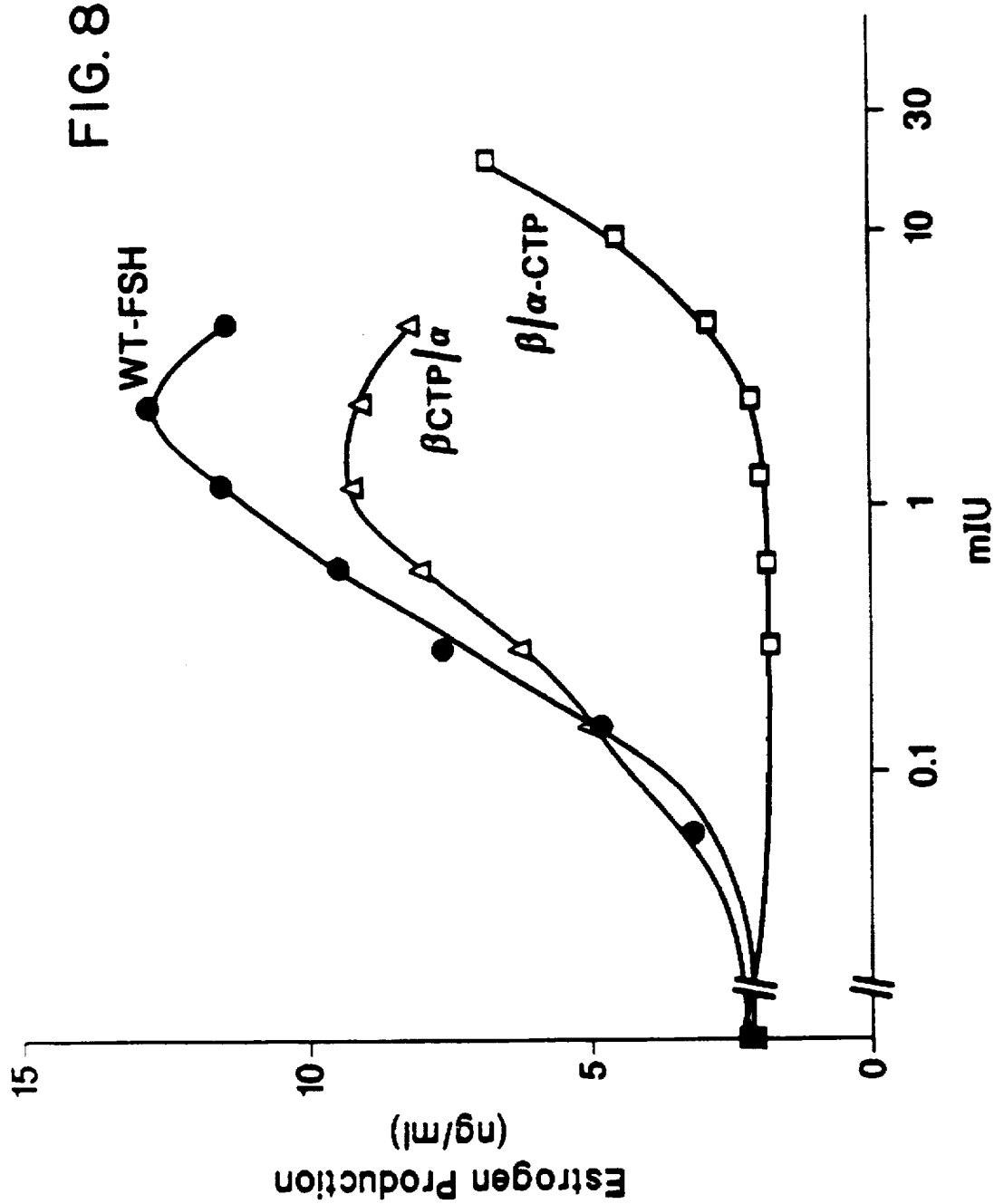
FIG. 8 is a graph showing the in vitro biological activity of native FSH and FSH containing either an extended β subunit or αC or both.

FIG. 8 compares the steriodogenic response of wild type recombinant FSH, (closed circles) αC-FSHβ (open squares), and FSH β-CTP subunit/α (open triangles). It is seen that the presence of CTP on the carboxy end of the α subunit results in a lower biologic response (25–50 fold reduction).

Figure 9:
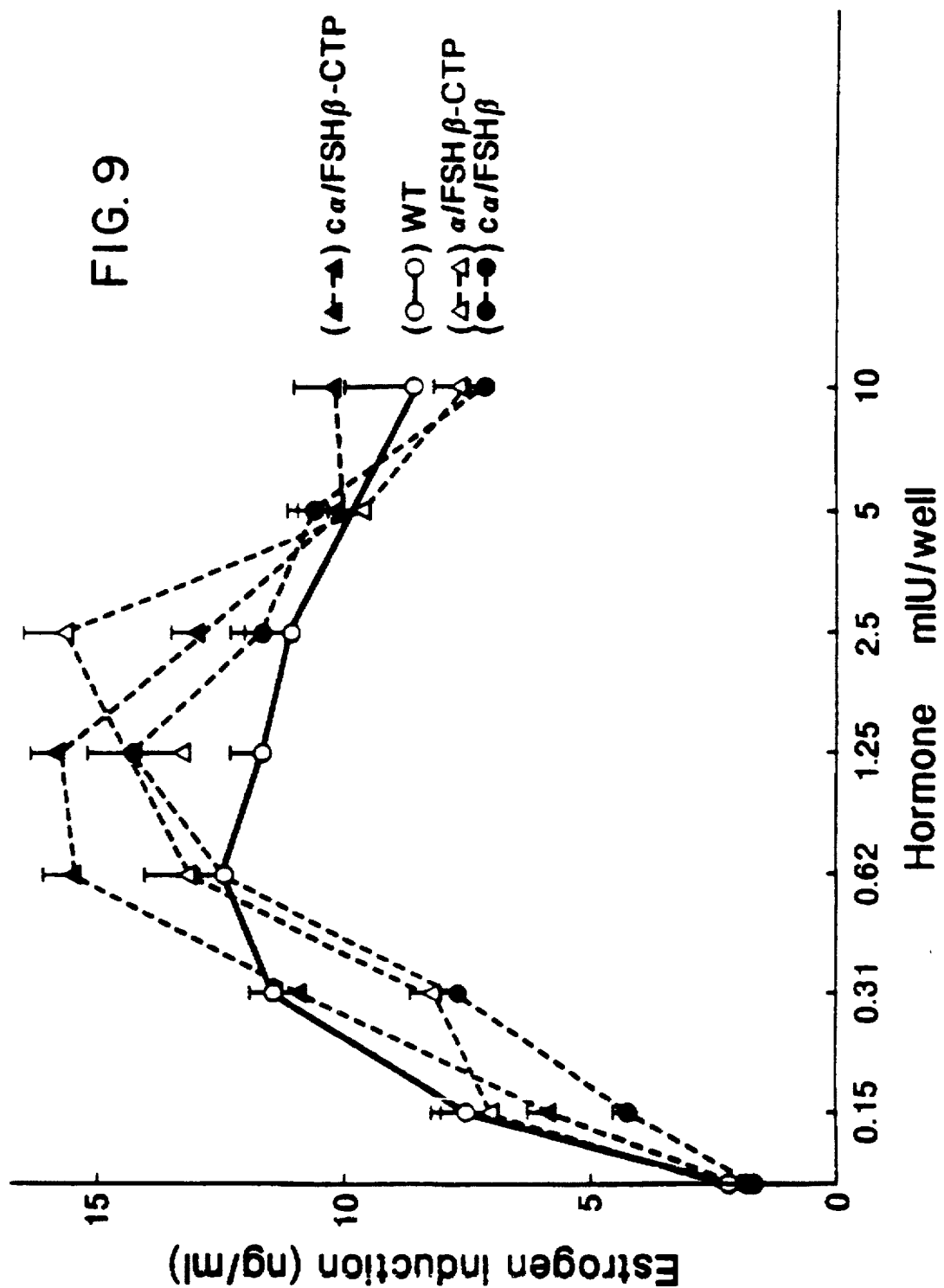
FIG. 9 is a graph showing in vitro biological activity of native FSH and FSH containing Cα or both.

In contrast, the presence of the CTP on the amino end of the α subunit (Cα) did not affect receptor binding or steroidogenesis (FIG. 9) of FSH dimers. Unmodified recombinant FSH (open circles), FSHβ extended at the carboxy terminus with a CTP unit dimerized with unmodified α (open triangles), FSHβ subunit dimerized with Cα (closed circles), and CTP-extended βFSH dimerized with Cα (closed triangles) all show similar activities. The modified forms at optimum concentration show somewhat higher activities than the unmodified forms. Preliminary results show Cα dimers will provide long acting agonists with biological activity comparable to the native hormone.

Further results showed that modified proteins including partial CTP sequences particularly those lacking O-linked sites elicit a biologic response comparable to dimers that include full length CTP and are expected to be less antigenic.

I claim:

1. A modified protein or peptide, wherein said modification comprises extension of the amino terminus of said protein or peptide with the amino acid sequence of the carboxy terminal portion (CTP) of human CGβ subunit, said CTP corresponding to the amino acid sequence from positions 112–118 to position 145 of said CGβ subunit or a partial variant CTP unit which contains at least two glycosylation sites of said CTP with the proviso that the modified protein or peptide retains the biological activity of the unmodified form thereof and is other than a subunit of a glycoprotein selected from the group consisting of luteinizing hormone, follicle stimulating hormone, thyroid stimulating hormone, and chorionic gonadotropin.

2. The modified peptide or protein of claim 1 wherein said CTP unit contains all four glycosylation sites (sites 1, 2, 3 and 4) found in native CTP unit.

3. The modified peptide or protein of claim 1 wherein the glycosylation sites in said partial or variant CTP unit consist of sites 1, 2 and 3; or sites 1, 3 and 4; or sites 1, 2 and 4; or sites 2, 3 and 4.

4. The modified peptide or protein of claim 1 wherein the glycosylation sites in said partial or variant CTP unit consist of sites 1 and 2; or sites 1 and 3; or sites 1 and 4; or sites 2 and 3; or sites 2 and 4; or sites 3 and 4.

5. The modified peptide or protein of claim 1 wherein said partial CTP unit consists of positions 112–132; 115–132; 116–132; or 118–132; or 112–127; 115–127; 116–127; or 118–127.

6. The modified peptide or protein of claim 1 wherein said peptide or protein is a cytokine.

7. The modified peptide or protein of claim 6 wherein said peptide or protein is IL-3.

8. A pharmaceutical composition comprising the modified protein or peptide of claim 1 in admixture with a pharmaceutically acceptable excipient.

9. A recombinant expression system which comprises a nucleotide sequence encoding the modified protein or peptide of claim 1 operably linked to control sequences to effect expression in a recombinant host cell.

10. The expression system of claim 9 wherein said modified protein or peptide is a cytokine.

11. The expression system of claim 10 wherein said cytokine is IL3.

12. A recombinant host cell modified to contain the expression system of claim 9.

13. The host cell of claim 12 wherein the modified protein or peptide is a cytokine.

14. The host cell of claim 13 wherein the cytokine is IL3.

15. A method to produce a modified protein or peptide, wherein said modification comprises extension of the amino terminus of said protein or peptide with the amino acid sequence of the carboxy terminal portion (CTP) of human CGβ subunit, said CTP corresponding to the amino acid sequence from positions 112–118 to position 145 of said CGβ subunit or a partial or variant CTP unit which contains at least two glycosylation sites of said CTP with the proviso that the modified protein or peptide retains the biological activity of the unmodified form thereof and is other than a subunit of a glycoprotein selected from the group consisting of luteinizing hormone, follicle stimulating hormone, thyroid stimulating hormone, and chorionic gonadotropin which method comprises culturing the host cells of claim 12 under conditions wherein said modified protein or peptide is produced.

16. The method of claim 15 wherein the modified protein or peptide is a cytokine.

17. The method of claim 16 wherein the cytokine is IL3.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..12

( x i ) SEQUENCE DESCRIPTION: SEQ ID NO:1:

```
GAA  ATG  AAA  GAA  TAAA                                                16
Glu  Met  Lys  Glu
  1
```

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Glu  Met  Lys  Glu
  1
```

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..21

( x i ) SEQUENCE DESCRIPTION: SEQ ID NO:3:

```
CAG  GAC  TCC  TCT  TCC  TCA  AAG                                       21
Gln  Asp  Ser  Ser  Ser  Ser  Lys
  1                    5
```

( 2 ) INFORMATION FOR SEQ ID NO:4:

( i ) SEQUENCE CHARACTERISTICS:
( A ) LENGTH: 7 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Gln  Asp  Ser  Ser  Ser  Ser  Lys
  1                    5
```

( 2 ) INFORMATION FOR SEQ ID NO:5:

( i ) SEQUENCE CHARACTERISTICS:
( A ) LENGTH: 16 base pairs (B) TYPE: nucleic acid
(C) STRANDEDNESS: single
(D) TOPOLOGY: linear (ix) FEATURE:
(A) NAME/KEY: CDS
(B) LOCATION: 1..12

(xi) SEQUENCE DESCRIPTION: SEQ ID NO:5:

```
GAA ATG AAA GAA GCTT                                             16
Glu Met Lys Glu
  1
```

(2) INFORMATION FOR SEQ ID NO:6:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:6:

```
Glu Met Lys Glu
  1
```

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ix) FEATURE:
(A) NAME/KEY: CDS
(B) LOCATION: 1..21

(xi) SEQUENCE DESCRIPTION: SEQ ID NO:7:

```
CAG GAA GCT TCT TCC TCA AAG                                      21
Gln Glu Ala Ser Ser Ser Lys
  1               5
```

(2) INFORMATION FOR SEQ ID NO:8:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:8:

```
Gln Glu Ala Ser Ser Ser Lys
  1               5
```

(2) INFORMATION FOR SEQ ID NO:9:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(A) NAME/KEY: CDS
(B) LOCATION: 1..27

(xi) SEQUENCE DESCRIPTION: SEQ ID NO:9:

```
GAA ATG AAA GAA GCT TCT TCC TCA AAG                              27
Glu Met Lys Glu Ala Ser Ser Ser Lys
```

(2) INFORMATION FOR SEQ ID NO:10:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:10:

```
Glu Met Lys Glu Ala Ser Ser Ser Lys
 1               5
```

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..27

(xi) SEQUENCE DESCRIPTION: SEQ ID NO:11:

```
GAA ATG AAA GAA TCC TCT TCC TCA AAG                        27
Glu Met Lys Glu Ser Ser Ser Ser Lys
 1               5
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: protein (xi) SEQUENCE DESCRIPTION: SEQ ID NO:12:

```
Glu Met Lys Glu Ser Ser Ser Ser Lys
 1               5
```

(2) INFORMATION FOR SEQ ID NO:13:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:13:

```
Ser Ser Ser Ser Lys Ala Pro Pro Pro Ser Leu Pro Ser Pro Ser Arg
 1               5                   10                  15
Leu Pro Gly Pro Ser Asp Thr Pro Ile Leu Pro Gln
                20                  25
```

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

```
GCCTTTGAGG AAGAGGAAGA TTTGTGATAA TAAC                      34
```

( 2 ) INFORMATION FOR SEQ ID NO:15:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GTTATTATCA CAAATCTTCC TCTTCCTCAA AGGC        34

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GTAAAACGAC GGCCAGT        17

( 2 ) INFORMATION FOR SEQ ID NO:17:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AACAGCTATG ACCATG        16

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

AGCGGATAAC AATTTCACAC AGGA        24

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CATTCCGCTC CTGATTCCTC TTCCTCAAAG        30

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

CTTTGAGGAA GAGGAATCAG GAGCGGAATG        30

( 2 ) INFORMATION FOR SEQ ID NO:21:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:21:

CCGATCCTCC CACAAGTGCA GGATTGCCCA        30

( 2 ) INFORMATION FOR SEQ ID NO:22:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:22:

TGGGCAATCC TGCACTTGTG GGAGGATCGG        30

( 2 ) INFORMATION FOR SEQ ID NO:23:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:23:

AAAGCTTCTG GGGATCTTGA GGTTCTTA        28